United States Patent
Beyerlein et al.

(10) Patent No.: US 7,613,273 B2
(45) Date of Patent: Nov. 3, 2009

(54) APPARATUS WITH A MOVING SYSTEM AND A STATIONARY SYSTEM

(75) Inventors: Walter Beyerlein, Bubenreuth (DE); Johann Kolar, Zürich (CH)

(73) Assignee: Siemens Aktiengesellschaft, Munich (DE)

( * ) Notice: Subject to any disclaimer, the term of this patent is extended or adjusted under 35 U.S.C. 154(b) by 507 days.

(21) Appl. No.: 11/649,138

(22) Filed: Jan. 3, 2007

(65) Prior Publication Data

US 2007/0177326 A1    Aug. 2, 2007

(30) Foreign Application Priority Data

Jan. 12, 2006    (DE) .................. 10 2006 001 671

(51) Int. Cl.
    *H05G 1/60* (2006.01)
    *A61B 6/03* (2006.01)
(52) U.S. Cl. ..................... 378/4; 378/901; 361/143
(58) Field of Classification Search ............ 378/4, 378/11, 21, 23–26; 361/143
    See application file for complete search history.

(56) References Cited

U.S. PATENT DOCUMENTS

| | | | |
|---|---|---|---|
| 3,569,791 A * | 3/1971 | Vogel | 361/143 |
| 4,342,001 A * | 7/1982 | Sauer | 330/9 |
| 4,866,556 A * | 9/1989 | Hebenstreit | 361/91.1 |
| 4,878,244 A * | 10/1989 | Gawargy | 379/402 |
| 5,161,083 A * | 11/1992 | Mohler et al. | 361/143 |
| 5,644,254 A * | 7/1997 | Boudry | 326/62 |
| 7,254,210 B2 * | 8/2007 | Popescu | 378/19 |
| 7,263,330 B2 * | 8/2007 | Wuidart | 455/41.1 |
| 7,355,833 B2 * | 4/2008 | Kozaki | 361/139 |
| 7,436,925 B2 * | 10/2008 | Manzke et al. | 378/8 |
| 2003/0068006 A1 * | 4/2003 | Beyerlein et al. | 378/15 |
| 2007/0280405 A1 * | 12/2007 | Krumme et al. | 378/4 |
| 2008/0095314 A1 * | 4/2008 | Katcha et al. | 378/101 |

\* cited by examiner

*Primary Examiner*—Christopher W Fulton
(74) *Attorney, Agent, or Firm*—Brinks, Hofer, Gilson & Lione

(57) ABSTRACT

An apparatus includes a first, stationary system, in particular a stator, and a second system which is provided for moving relative to the first system, in particular an armature, a first and second electrical reference potentials which are assigned to the first system and the second system, respectively, and a coupler for potential coupling of the two reference potentials. The coupler is used for the potential coupling of a ground of the moving system to a ground of the stationary system in order to ensure a reliable data transmission between the systems. In order to achieve a coupling with a maximal service life and requires minimal maintenance, the coupler has a field coupling component for mechanically contactless potential coupling.

18 Claims, 1 Drawing Sheet

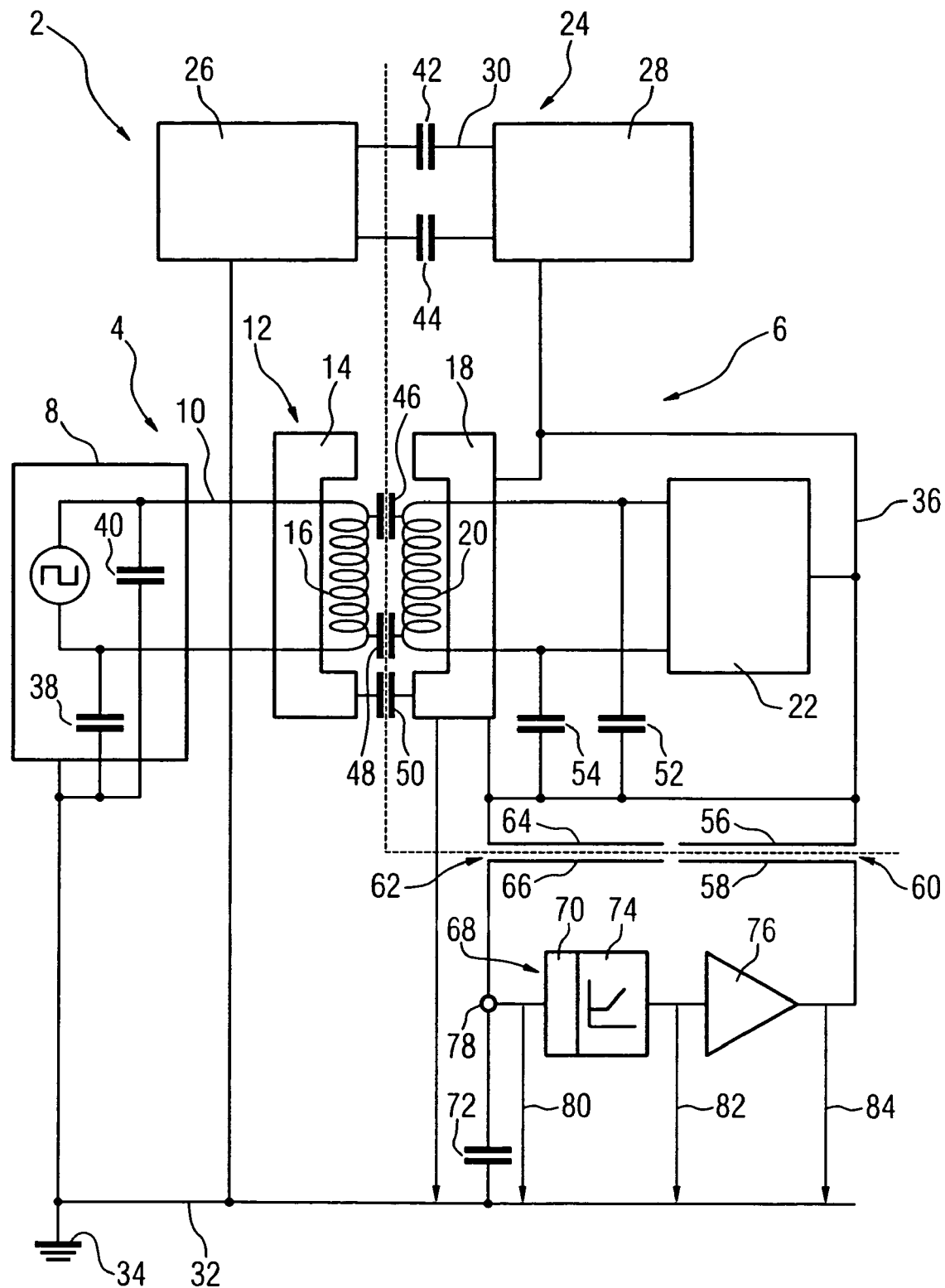

APPARATUS WITH A MOVING SYSTEM AND A STATIONARY SYSTEM

The present patent document claims the benefit of the filing date of DE 10 2006 001 671.8 filed Jan. 12, 2006, which is hereby incorporated by reference.

BACKGROUND

The present embodiments relate to an apparatus with a moving system and a stationary system.

Generally, a large medical device such as a computer tomography system includes a stationary system and a moving system. A large generator may require data transmission from the stationary system to the moving system and back.

Data transmission may take place via a conductive or capacitive coupling. The two systems must each have a reference ground with a substantially identical potential. In the case of differential data transmission, such a potential equivalence is advantageous since, as a result of the maximum permitted common-mode level and frequency-dependent common-mode suppression, potential differences that allow data transmission are subject to limits. Potential differences in the systems can be caused by a current flow in the impedance of the connection of the two reference systems. This current flow can be produced via parasitic capacitances, for example, by a power supply that supplies energy to the moving system.

Slip rings or electrically conductive bearings or purlins for coupling the two reference grounds may be used. If the moving system has only limited path movement, use is made of, for example, mobile conductors. Slip-ring connections are subject to wear at the carbons and on the path of travel and result in environmental dirt accumulation. Ball bearings can result in an inadequate coupling. Mobile conductors under continuous load are susceptible to breakage.

SUMMARY

The present embodiments may obviate one or more of the limitations or drawbacks inherent in the related art. For example, in one embodiment, an apparatus comprises a stationary system and a system that moves relative to said stationary system, and allows a continuous and reliable potential coupling of reference potential sensors.

In one embodiment, an apparatus includes a first system, for example, a stator, and a second system, which moves relative to the first system, for example, an armature. A first electrical reference potential sensor is assigned to the first system and a second electrical reference potential sensor is assigned to the second system. A coupler is operable for potential coupling of the two reference potential sensors.

In one embodiment, the coupler includes a field coupling component for mechanically contactless potential coupling. It is possible to achieve a wear-free and maintenance-free coupling of the reference potentials. The coupler connects with a contactless energy supply of the moving system and a data transmission. The reference potential sensor of the stationary system or, for example, of the armature may be grounded or be an electrical ground connection. The reference potential sensor of the moving system or armature corresponds to a ground connection, but does not have a direct contact to the electrical ground. The potential of the moving system does not have to be identical to the ground potential. The coupler is connected in an electrically conductive manner to the reference potential sensor of the armature.

In one embodiment, a field coupling component allows coupling of an electrical or magnetic variable, particularly a potential, via a field, for example, an electrical or magnetic field. As a result of the potential coupling, the two reference potentials are coupled together in any suitable manner. For example, in one embodiment, one potential may have an influence on the other potential. In this embodiment, the potentials may be made reciprocally dependent.

The present embodiments may be used, for example, with a computer tomography system, which transmits large amounts of data from the armature to the stator and vice versa. The present embodiments are also suitable for all rotational machines and for devices in which the armature is moved rotationally or translationally relative to the stator.

In one embodiment, the field that is utilized for coupling may be a magnetic field when an inductive coupling component is used. However, the creation of a magnetic field, for example, a high-frequency magnetic field, as a coupling field requires a certain energy and has a relatively high impedance.

In one embodiment, a coupling, which has a low impedance, can be achieved by using an electrical field. In this embodiment, the field coupling component is a capacitive element, for example, a capacitor. The potential coupling may be rapidly controlled using a low impedance. The potential coupling is suitable for high frequencies, for example, frequencies in the range of the data transmission frequencies. By applying an electrical voltage at the capacitor and creating an electrical coupling field in the capacitor, the reference potential of the moving system is influenced.

In one embodiment, the coupler is arranged at least partly on an external wall of the armature, in for example, on the outside of the external wall. In one embodiment, a large-surface capacitive element is implemented. The large-surface capacitive element has two opposing metal surfaces on the armature and on the stator.

In one embodiment, the apparatus includes a measuring device that measures a measured variable. The measured variable identifies a potential difference between the reference potential sensors. An unwanted potential difference between the reference potential sensors may be detected and actions taken to counter the unwanted potential difference. The measured variable can identify the potential difference between the reference potential sensors directly, for example, as a direct proportion, or indirectly, for example, by use of further variables.

The potential difference can be captured reliably and without susceptibility to error if the measuring device is provided for capturing a potential difference at the first reference potential sensor as a measured variable. The first reference potential sensor is directly grounded or is connected to a fixed ground. The potential difference may be measured directly by measuring a voltage at the reference potential sensor. If the potential difference is measured by measuring a current which flows from or to the measuring component, for example, a capacitive element, rapid changes of the potential difference between the reference potential sensors can be captured effectively.

In one embodiment, the measuring device includes a measuring component, which is implemented according to the same principle as the field coupling component. For example, the field coupling component and the measuring component are embodied as capacitors.

In one embodiment, the coupler is connected to the reference potential sensor of the stationary system in an electrically conductive manner. In another embodiment, the measuring device has a separation capacitor for decoupling at the first reference potential sensor. The separation capacitor can be realized as a base capacitor and serves as a capacitive measuring separator. Alternatively, the measuring device may be decoupled from the reference potential sensor by a high-impedance measuring amplifier.

In one embodiment, the coupling capacitor, which is located between the armature and the stator, has a capacitance that is relatively small. The coupling capacitor has limited electrode surfaces and a significant distance between the electrodes due to mechanical tolerances. The limited electrode surfaces and/or significant distance results in a significant impedance, which would have an interfering effect on the potential coupling due to the associated high current. The impedance may be restricted if the apparatus has an amplifier that amplifies a coupling variable, which is supplied to the field coupling component, for example, a voltage or a current which is applied to the field coupling component. The amplifier makes it possible to increase, for example, an effective capacitance of the field coupling component.

In one embodiment, a regulator is provided in the apparatus. The regulator adjusts a coupling variable of the coupler. The potential equalization between the reference potential sensors can take place particularly simply and autonomously. The coupling variable can be the adjustment variable that is regulated. The coupling variable may also be adjusted indirectly by the regulator via a further adjustment variable, for example, if the regulator is connected in series after an amplifier. The regulating variable can be the potential difference between the reference potential sensors or the measured variable, which is directly or indirectly linked to the potential difference.

The regulator is configured to manage changes in the capacitances of the coupler and/or measuring device. The regulator prevents changes in the capacitances from having an effect on the minimum potential difference between the stationary and the moving system.

BRIEF DESCRIPTION OF THE DRAWINGS

FIG. 1 illustrates one embodiment of a computer tomography system that includes a stationary system and a moving system.

DETAILED DESCRIPTION

The present embodiments are explained in greater detail with reference to the exemplary embodiment illustrated in FIG. 1. As shown in FIG. 1, an apparatus, which is illustrated for exemplary purposes as a computer tomography system 2, is illustrated as a circuit diagram.

In one embodiment, as shown in FIG. 1, a computer tomography system 2 includes a stationary system 4 and a moving system 6, which rotates at, for example, three rotations per second relative to the stationary system 4 during operation. The stationary system 4 has a bearing (not shown) for rotatable mounting of the moving system 6 relative to the stationary system 4.

In one embodiment, at least one inverter 8 that generates an alternating current is present on the stationary system 4. A conductor arrangement 10 supplies the alternating current to a contactless power transmission 12, which is a primary side 14 with at least one coil 16 on the stationary system 4 and a secondary side 18 with at least one coil 20 on the moving system 6. Electrical energy is transmitted via an inductive coupling from the primary side 14 to the secondary side 18 using an alternating magnetic field. The inductive coupling may be used for feeding loads 22, for example, an X-ray tube or a detector arrangement.

In one embodiment, information may be transmitted between the stationary system 4 and the moving system 6. In this embodiment, a data transmission device 24 includes a first unit 26 in the stationary system 4 and a second unit 28 in the moving system. The first unit 26 and second unit 28 are connected to a transmission line 30, which functions in a contactless manner.

In one embodiment, the first unit, conductor arrangement, and inverter are connected to a first reference potential sensor 32, which is connected to ground 34. The first reference potential sensor 32 is operable to ensure a consistent working potential of the devices of the stationary system 4. The first unit, conductor arrangement, and inverter are thus connected to the ground 34 as a reference potential. In one embodiment, the moving system 6 includes a reference potential sensor 36, which is not directly electrically connected to the reference potential sensor 32 of the stationary system 4 due to the motional freedom of the moving system 6 that defines a separate reference potential, which may vary from the ground 34.

In one embodiment, during operation, in addition to real capacitances, the computer tomography system 2 also has parasitic capacitances 38-54 at which potentials are created by the flowing currents. The parasitic capacitances 38-54 influence the reference potential of the stationary system 4 or moving system 6 to which they belong. The parasitic capacitances 38-54 may cause a potential shift of the reference potential of the moving system 6 such that a transmission of information by the data transmission 24 is disrupted or rendered impossible. To reduce the potential shift of the reference potential of the moving system 6, a large metal surface 56, which is disposed on an external surface of the moving system 6 and measures approximately 20 cm×50 cm, is located opposite to a metal surface 58 of at least the same size on the external surface of the moving system 6. The metal surfaces 56, 58 are approximately 0.1 mm apart and form a coupler 60, which is embodied as a field coupling component in the form of a capacitance and couples the reference potential of the moving system 6 to the reference potential of the stationary system 4 via an electrical field.

In one embodiment, a further capacitive element, which includes two metal surfaces 64, 66, is provided on the external surfaces and forms a measuring component 62 that is connected to the measuring device 68. The measuring device 68 includes a measured value capturing unit 70 and a separation capacitor 72 as a decoupler. A regulator 74 is connected to the measuring device 68. An amplifier 76 is connected to the regulator 74. The amplifier 76 may be embodied as a power amplifier, which is electrically connected to the metal surface 58 of the coupler 60.

During operation of the computer tomography system 2, the reference potential of the reference potential sensor 36 may vary from the grounded reference potential of the stationary system 4 and have a voltage relative to the grounded reference potential. This causes a shift of loads in the measuring component 62, as a result of which a measuring point 78—dependent on the decoupler 72—illustrates a voltage at the grounded reference potential. This voltage may be captured by the measuring device 68 as a measured value 80, which has a known ratio to the potential difference between the reference potentials.

In one embodiment, the measured value is used by the regulator 74 as a regulating variable, which produces a corresponding adjustment variable 82 that is amplified by the amplifier 76 and is passed to the coupler 60 as a coupling variable 84. An electrical field is consequently generated between the metal surfaces 56, 58 and causes a load shift in the field coupling component. The load shift has a known influence on the reference potential of the moving system 6. In this way—with the aid of suitable regulation and amplification—the reference potential of the reference potential sensor 36 is influenced so that the potential difference between the two reference potentials of the two systems 4, 6 is as small as possible. As a result of the small potential difference between the two systems 4, 6, it is possible to ensure effective transmission of information by the data transmission 24.

In one embodiment, the measured value 80 may be measured as a potential difference, for example, a voltage at the grounded reference potential of the stationary system 4, whereby at least essentially static potential differences between the reference potential sensors 32, 36 can also be captured.

In one embodiment, the data transmission 24 is disrupted by the dynamic potential differences whose fluctuation frequencies lie in the frequency range of the information transmission. However, high-frequency potential differences may in some circumstances result in only minor load shifts, and therefore only small voltages may be measured at the measuring point 78. In this embodiment, it may be beneficial to capture the current that flows through the measuring point 78 as a measured value, which can have a known ratio to a potential shift of the reference potential sensor 36. This measured value can be used for adjustment of the adjustment variable 82 such that in the case of a potential shift the reference potential may already be corrected and the potential shift can therefore be counteracted, without requiring a significant potential difference between the systems 4, 6.

The invention claimed is:

1. An apparatus comprising:
a stationary system;
a moving system, which is operable to move relative to the stationary system;
a first reference potential assigned to the stationary system, and a second reference potential assigned to the moving system; and
a coupler that is operable to potential couple the first and second reference potentials,
wherein the coupler includes a field coupling component for mechanically contactless potential coupling.

2. The apparatus as claimed in claim 1, wherein the coupler comprises a capacitive element.

3. The apparatus as claimed in claim 1, wherein the coupler is disposed at least partly on an external wall of the moving system.

4. The apparatus as claimed in claim 1, further comprising a measuring device that is operable to measure a measured variable, which identifies a potential difference between the first and second reference potentials.

5. The apparatus as claimed in claim 4, wherein the measuring device is operable to capture a potential difference at the first reference potential as the measured variable.

6. The apparatus as claimed in claim 5, wherein the measuring device includes a measuring component, which operates according to a same principle as the field coupling component.

7. The apparatus as claimed in claim 6, wherein the measuring component and field coupling component are capacitors.

8. The apparatus as claimed in claim 7, wherein the measuring component comprises a first metal surface and a second metal surface located opposite to the first metal surface.

9. The apparatus as claimed in claim 8, wherein the first and second metal surfaces are approximately 20 cm×50 cm, and wherein the first and second metal surfaces are approximately 0.1 mm apart.

10. The apparatus as claimed in claim 4, wherein the measuring device comprises a separation capacitor that is operable to decouple the first reference potential.

11. The apparatus as claimed in claim 4, further comprising an amplifier that is operable to amplify a coupling variable, which is supplied to the field coupling component.

12. The apparatus as claimed in claim 11, further comprising a regulator that is operable to adjust the coupling variable of the coupler.

13. The apparatus as claimed in claim 12, wherein the regulator is configured to manage changes in the capacitances of the coupler and/or measuring device.

14. The apparatus as claimed in claim 1, wherein the apparatus is a computer tomography system.

15. The apparatus as claimed in claim 1, wherein the stationary system comprises a stator and the moving system comprises an armature.

16. The apparatus as claimed in claim 1, wherein the field coupling component comprises a first metal surface and a second metal surface located opposite to the first metal surface, and wherein the first and second metal surfaces are approximately 0.1 mm apart.

17. The apparatus as claimed in claim 16, wherein the first and second metal surfaces are approximately 20 cm×50 cm.

18. The apparatus as claimed in claim 1, comprising a data transmission device that includes a first unit in the stationary system and a second unit in the moving system, wherein the first unit and second unit are connected to a transmission line, which is operable to transmit data between the first unit and second unit in a contactless manner.

* * * * *